United States Patent
Deller et al.

(10) Patent No.: US 7,443,946 B2
(45) Date of Patent: Oct. 28, 2008

(54) METHODS AND APPARATUS FOR 4DCT IMAGING SYSTEMS

(75) Inventors: Timothy Wayne Deller, Waukesha, WI (US); Kelly Lynn Piacsek, Pewaukee, WI (US); Steven Gerald Kohlmyer, Lynnwood, WA (US)

(73) Assignee: General Electric Company, Schenectady, NY (US)

( * ) Notice: Subject to any disclaimer, the term of this patent is extended or adjusted under 35 U.S.C. 154(b) by 283 days.

(21) Appl. No.: 11/401,087

(22) Filed: Apr. 10, 2006

(65) Prior Publication Data

US 2007/0237289 A1   Oct. 11, 2007

(51) Int. Cl.
    *A61B 6/03* (2006.01)
(52) U.S. Cl. ......................................................... 378/8
(58) Field of Classification Search ............... 378/4, 378/8; 382/128, 131
    See application file for complete search history.

(56) References Cited

U.S. PATENT DOCUMENTS 3,608,545 A * 9/1971 Novack et al. ............. 600/513
3,871,360 A * 3/1975 Van Horn et al. ............ 378/95
6,421,552 B1 * 7/2002 Hsieh .............................. 378/8
7,182,083 B2 * 2/2007 Yanof et al. .................. 600/428
2003/0152189 A1 * 8/2003 Li et al. ........................... 378/8
2004/0258286 A1   12/2004 Salla et al. .................... 382/128
2005/0201510 A1 * 9/2005 Mostafavi ....................... 378/8

OTHER PUBLICATIONS

Pan et al., "4D-CT imaging of a volume influenced by respiratory motion on multi-slice CT", Medical Physics, vol. 31, Issue 2, Feb. 2004, pp. 333-340.*
Author: Tinsu Pan; 2005 Am. Assoc. Phys. Med.; Comparison of helical and cine acquisitions for 4D-CT imaging with multislice CT; Date: Feb. 2005; pp. 627-634 (8 pages).
Author: Tinsu Pan et al.; 2005 Am. Assoc. Phys. Med.; Four-dimensional computer tomography: Image formation and clinical protocol; Date Apr. 2005; pp. 874-889 (16 pages).

* cited by examiner

*Primary Examiner*—Chih-Cheng G Kao
(74) *Attorney, Agent, or Firm*—Fisher Patent Group, LLC; Thomas M. Fisher

(57) ABSTRACT

A method includes receiving cine scan data, receiving a plurality of target phases of a periodic waveform, and generating a plurality of images, each image centered at one of the received target phases. A phase shall represent a percentage of a period of a repeating cycle.

18 Claims, 4 Drawing Sheets

US 7,443,946 B2

METHODS AND APPARATUS FOR 4DCT IMAGING SYSTEMS

BACKGROUND OF THE INVENTION

This invention relates generally to methods and apparatus for computed tomography (CT), and more particularly to methods and apparatus that facilitate 4DCT imaging.

4DCT respiratory imaging is an application designed to create a volume image data set representing the lungs and surrounding tissue throughout the respiratory cycle. Due to the nature of dynamic imaging, temporal resolution is important to the quality of the 4D reconstruction. This technology is primarily used for tumor identification and delineation for radiation therapy planning. Other uses include lung function imaging for detection of Chronic Obstructive Pulmonary Disease (COPD) and emphysema as well as vascular lung perfusion.

BRIEF DESCRIPTION OF THE INVENTION

In one aspect, a method includes performing a waveform analysis to detect an aberration and prompting a user when an aberration is detected.

In another aspect, a method includes receiving cine scan data, receiving a plurality of target phases of a periodic waveform, and generating a plurality of images, each image centered at one of the received target phases. A phase shall represent a percentage of a period of a repeating cycle.

In still another aspect, a system for reconstructing images is provided. The system includes a radiation source, a radiation detector positioned to receive radiation emitted from the source, and a computer coupled to the source and the detector. The computer is configured to receive scan data from the detector, extract a waveform from the scan data, and perform a temporal synchronization of the scan data using the extracted waveform.

In yet another aspect, a method includes receiving at least one target phase, scanning a periodic moving object to obtain at least one complete waveform of the periodic motion, and using the waveform to prospectively gate acquisitions around the target phase.

DETAILED DESCRIPTION OF THE INVENTION

Figure 1:
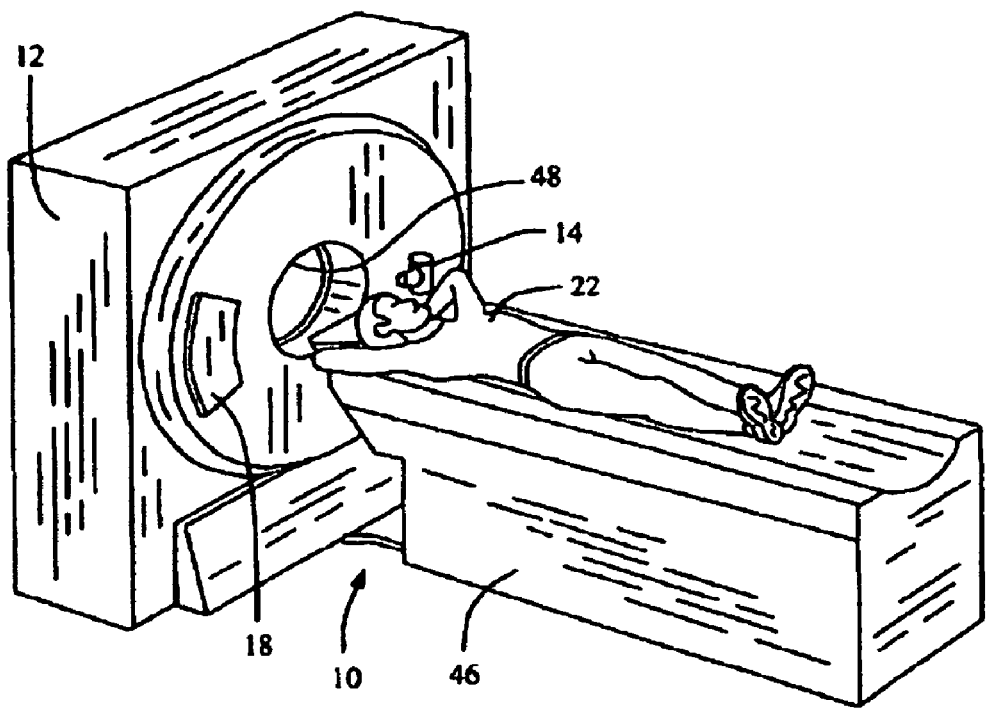
FIG. 1 is a pictorial view of a CT imaging system embodiment.

There are herein provided 4DCT image generation methods and apparatus useful for imaging systems such as, for example, but not limited to a Computed Tomography (CT) System. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to reconstruct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a display device.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images as well as scan data and view data representing a viewable image. However, many embodiments generate (or are configured to generate) at least one viewable image.

Figure 2:
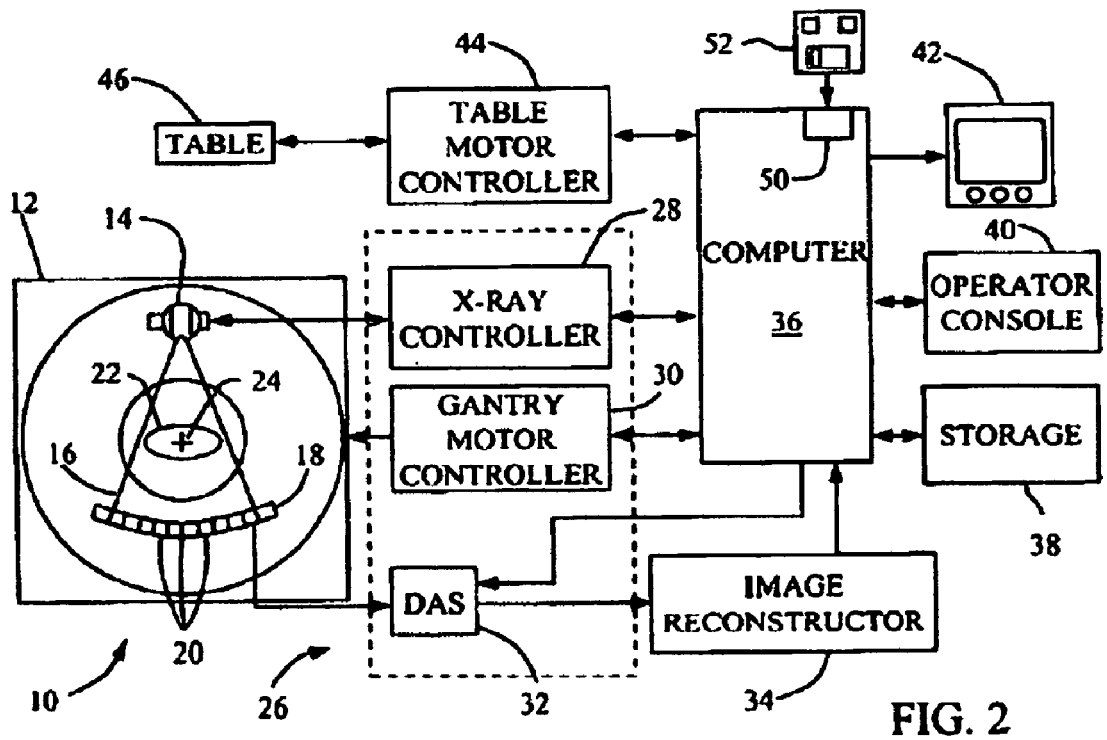
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12.

Detector array 18 is formed by a plurality of detector rows (not shown in FIGS. 1 and 2) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient 22. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 that stores the image in a mass storage device 38.

Computer 36 also receives commands and scanning parameters from an operator via a console 40 that has a keyboard. An associated cathode ray tube display 42 allows the operator to observe the reconstructed image and other data from computer 36. The operator supplied commands and parameters are used by computer 36 to provide control signals and information to DAS 32, radiation controller 28, and gantry motor controller 30. In addition, computer 36 operates a table motor controller 44 which controls a motorized table 46 to position patient 22 in gantry 12. Particularly, table 46 moves portions of patient 22 through gantry opening 48. In cine scan mode, table 46 is held stationary.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, computer 36 executes instructions stored in firmware (not shown). Generally, a processor in at least one of DAS 32, reconstructor 34, and computer 36 shown in FIG. 2 is programmed to execute the processes described below. Of course, the method is not limited to practice in CT system 10 and can be utilized in connection with many other types and variations of imaging systems. In one embodiment, Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center.

Figure 3:
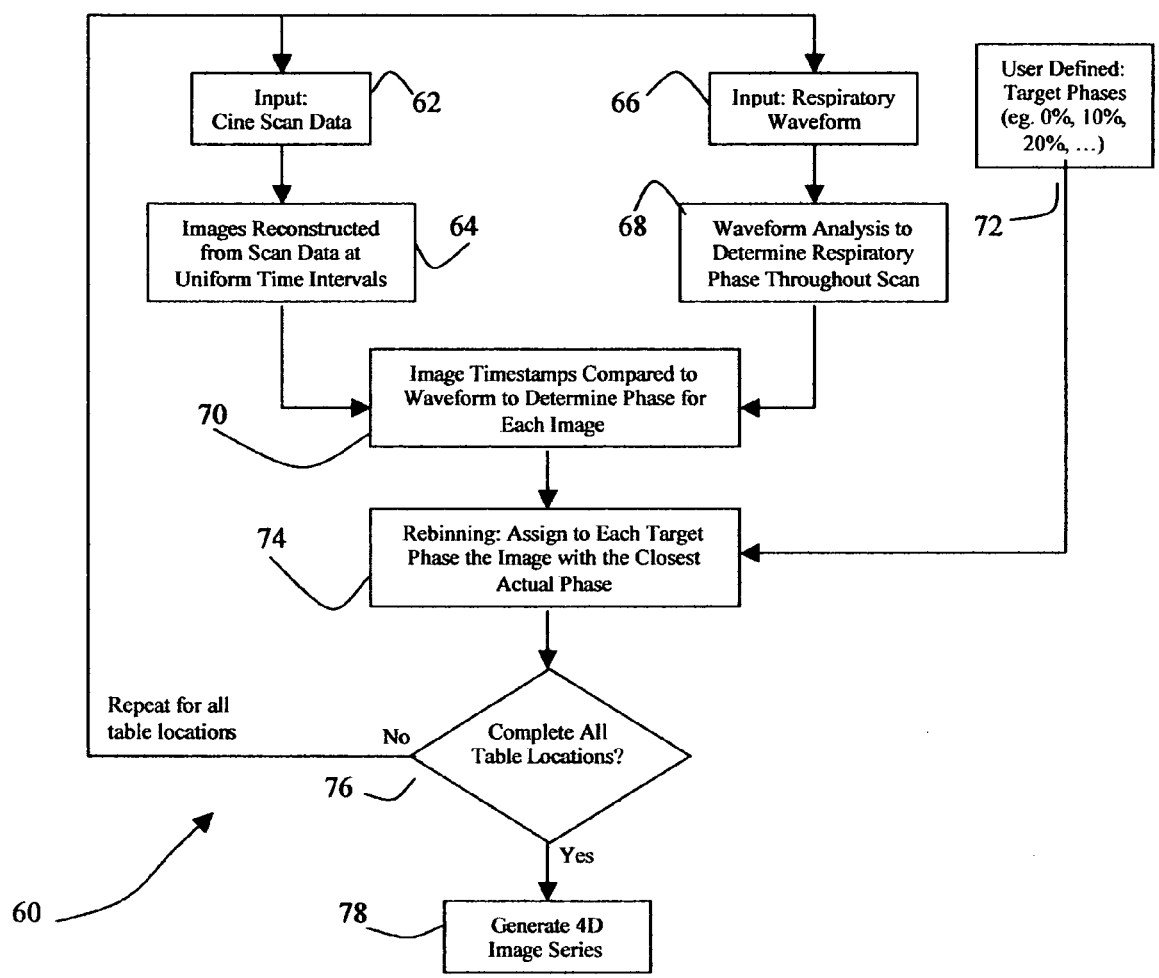
FIG. 3 illustrates a flowchart describing prior embodiment of a similar concept.

Existing methods in 4DCT respiratory imaging are found in the Advantage 4D software package commercially available from the GE Healthcare unit of the General Electric Company and summarized in a flowchart 60 of FIG. 3. Flowchart 60 includes inputting of cine scan data at step 62, and reconstruction of images from the scan data at uniform time intervals at step 64. A respiratory waveform recorded simultaneous to the acquisition of cine scan data (62) is inputted at step 66 and a waveform analysis to determine respiratory phase throughout the scan is done at step 68. At step 70 image timestamps are compared to the waveform to determine phases for each image. User defined target phases are inputted at step 72 and at step 74 rebinning is performed to assign to each user-requested target phase the image with the closest actual phase. A check is done at step 76 to determine if all table locations are completed and, if so, a 4D image series is generated at step 78. A 4D image series comprises an axial image at each phase time and each table location over the course of data acquisition. The 4D image series represents a single respiration cycle comprised of multiple breaths during scan acquisition.

The cine scan mode is utilized to acquire data during multiple gantry rotations for each fixed table location (one cine acquisition per table location). The table moves between each cine acquisition until the entire scan range is covered. The existing method generates a set of images uniformly distributed in time for each cine acquisition. Typically, the number of images is on the order of 10-15 images per table position and represent a time period greater than one respiratory cycle. To create 3D volumes throughout the respiratory period, the images are sorted into bins based on phase information derived from a respiratory waveform. This waveform can be obtained from a respiratory monitor or sensor (such as the Varian RPM-system commercially available from Varian Medical Systems, Inc, spirometric devices, piezoelectric sensors, strain gages, inductance plethysmographs, or mechanical sensors including ultrasound) or from the scan data itself as described in US Patent Application 2004/0258286 A1 by Salla, Avinash, Sirohey, and Pan. This process of grouping images based on respiratory phase is referred to as image rebinning, and each bin is defined by its target phase. By phase it is meant a percentage of a period of a repeating periodic cycle or motion. For example, a repeating respiration cycle.

The user may define the number of target phases, but typically ten target phases are defined from 0% to 90% in increments of 10%. The 0% phase (and 100% phase due to periodicity) corresponds to peak inspiration, and the 50% phase corresponds to peak expiration. Due to physiologic variability of the respiratory cycle, an image is not necessarily available at the exact target phase, resulting in a discrepancy between the target phase and the actual phase of the image. This discrepancy is referred to as the phase error.

Phase error may limit the quality of the 4D image series. In some cases, the same is used for two sequential target phases because no closer image exists for either target phase. This causes irregularity and temporal degradation of the 4D data set.

One approach available to improve these inconsistencies is simply to reconstruct a large number of images in the temporal dimension, perhaps on the order of 50-100 per cine acquisition. This would improve the issue of poor sampling in the temporal dimension. However, this approach requires increased reconstruction time and the generation of a very large number of images.

Therefore herein described are methods and apparatus that address the problem of phase error that occurs when retrospectively (meaning after the image data has been collected and reconstructed) rebinning a discretely sampled set of images into desired phases. The herein described methods and apparatus retrospectively reconstruct images centered at precisely specified time locations from cine scan data. The time locations correspond to a specific projection determined from externally recorded signals (such as the Varian RPM system) or signals derived from the scan data itself. The method is integrated into the reconstruction process to generate the exact images desired to maximize temporal precision and resolution.

Figure 4:
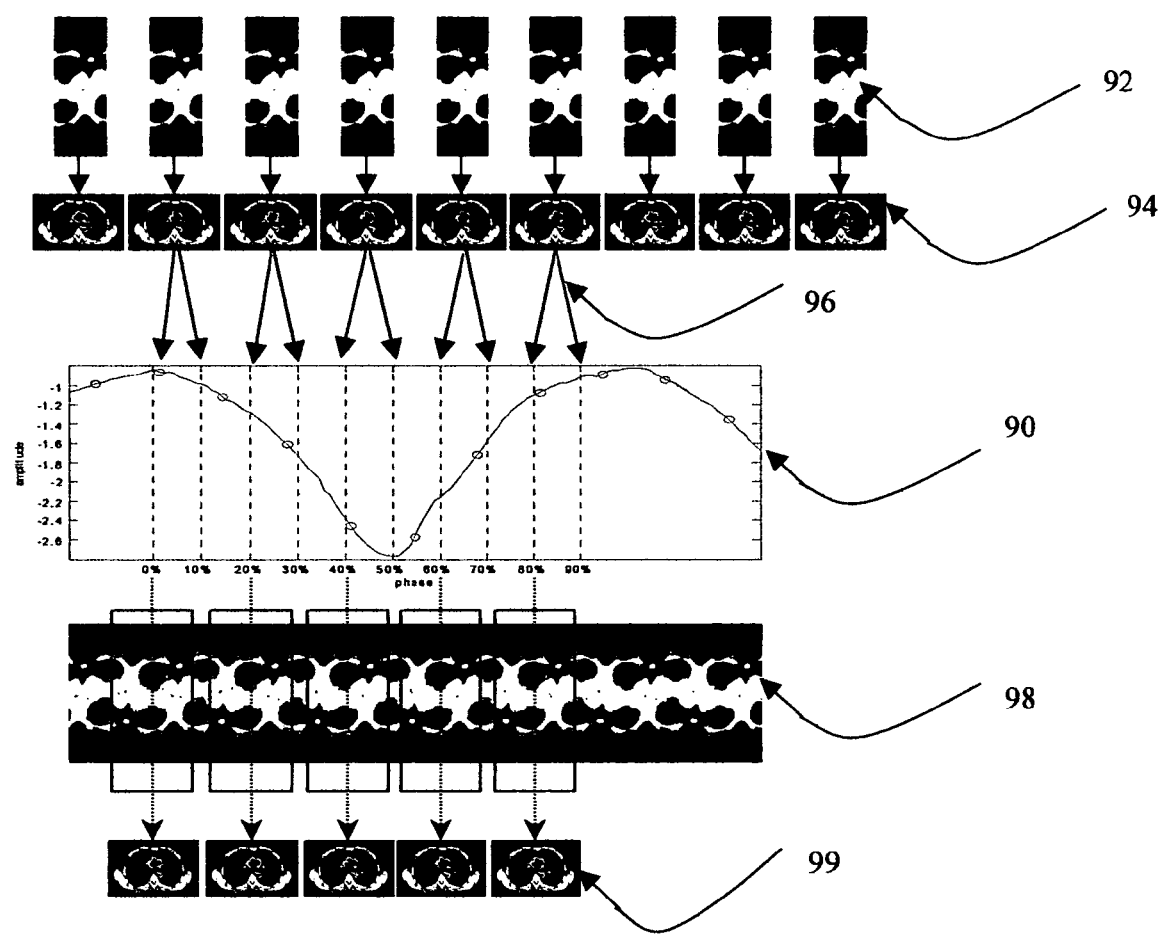
FIG. 4 illustrates graphically the old method from FIG. 3 and the new method of FIG. 5.
Figure 5:
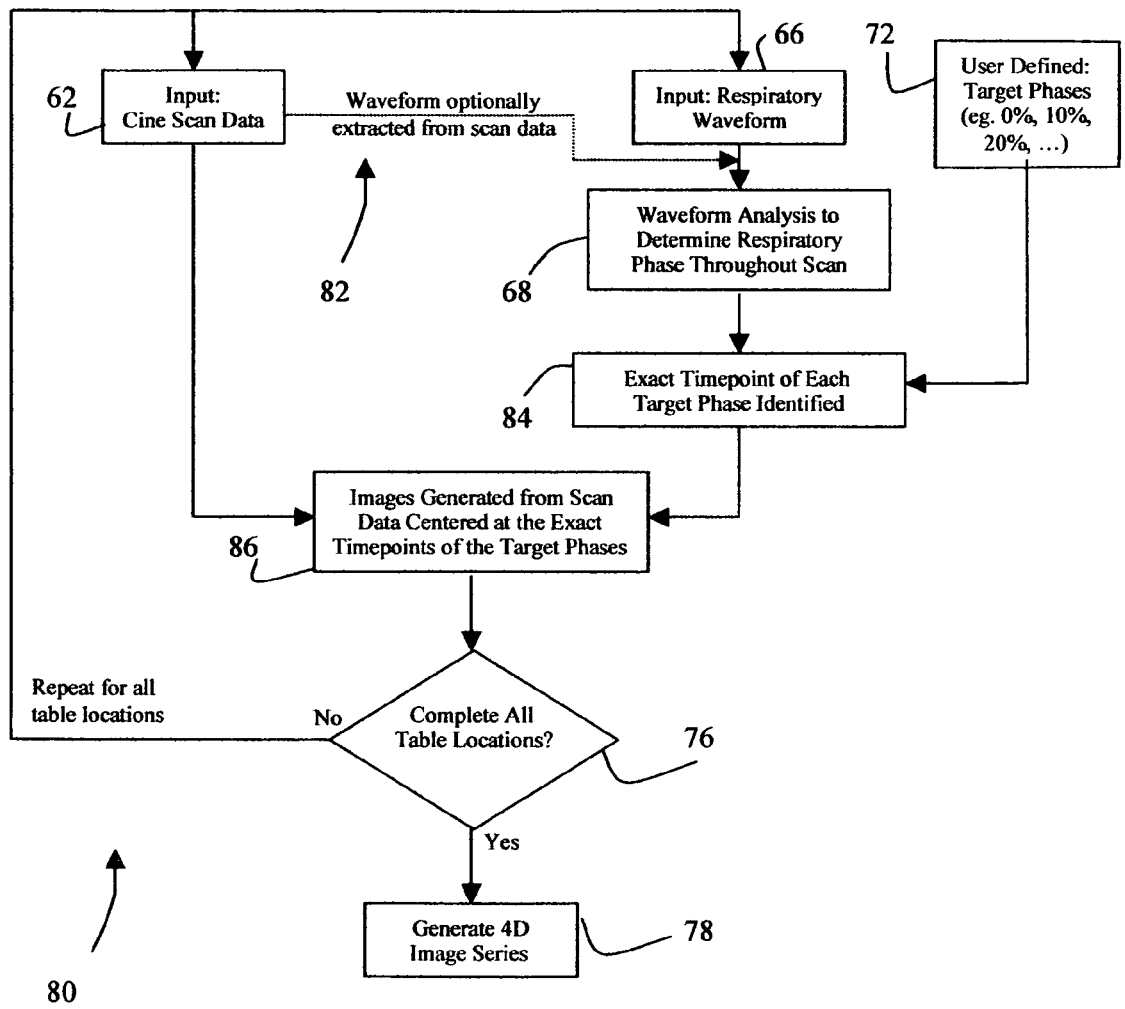
FIG. 5 is a flowchart describing the current invention.

Due to the nature of cine scan data, an image can be generated by extracting any consecutive block of views that spans enough data for half-scan (meaning less than a full rotation of view data to reconstruct an image, typically one-half the number of views) or full-scan (meaning a full rotation of view data) reconstruction. An image centered in time at any specified view can be generated provided that a sufficient number of views exist on either side of that time point to generate an image. FIG. 4 graphically illustrates this concept and the old concept. Both concepts utilize the target phases 90. The old concept used scan data 92 to generate multiple images 94, that were then linked 96 to the closest target phase 90. The new concept, as best shown in FIG. 5, but still referring to FIG. 4, uses the target phase 90 information on scan data 98 to generate perfectly matched images 99. The scan data necessary for half-scan reconstruction is centered about the desired target phase and falls between the solid lines in FIG. 4. The problem of phase error is eliminated using this approach because images are reconstructed at the exact phase locations desired.

This method is fundamentally different from the approach illustrated in FIG. 3. The herein described methods and apparatus generates images based on the target phase designation, whereas the method of FIG. 3 rebins existing images to the designated target phases. FIG. 5 is a flowchart presenting the proposed method 80. This flowchart can be compared to the flowchart in FIG. 3 to demonstrate the process differences. Method 80 includes inputting cine data 62 and user defined target phases 72. The waveform analysis 68 can be done on a waveform extracted 82 from the cine scan data itself. Method 80 also includes identifying the exact timepoint of each target phase at step 84 and generating images from the scan data centered at the exact timepoints of the target phases at step 86. Note that this approach provides flexibility to create a 4D series based on any trigger points (meaning signal of an event (or events) of interest, typically representing a target phase) in the respiratory signal. If a method other than phase grouping is preferred (such as motion or amplitude), then the method is easily adaptable to any waveform-based trigger.

The 4D processing in the existing method (FIG. 3) is performed on a workstation during a review session separate from the scan acquisition, and as a result, no method exists to replace the data from an irregular scan. Irregularities such as sighs, coughs, or an unusually long or short respiration during one or more acquisitions could greatly damage the reconstruction at the associated table locations. Because the proposed method (FIG. 5) is performed in the reconstruction chain on the scanner console, waveform analysis can be immediately performed to identify aberrant respiratory patterns during acquisition. As a result, the cine scan at the irregular table locations should be either shifted slightly in phase to compensate for the motion, or re-acquired altogether. This capability is available in the scanning protocol as an optional extension to the standard scan protocol.

One technical effect is that using the method of FIG. 5 results in 4D respiratory reconstructions that are smoother, more accurate, and improved in the temporal dimension, with the elimination of some causes for phase error.

Eliminating phase error improves synchronization between the separate table locations, contributing to an improved 3D reconstruction for any fixed phase. Resultantly, artifacts are reduced, and this is another technical effect.

The above advantages are possible with no changes in the amount of dose or to the scanning method. As a result, scan data from this relatively high dose application will be more frequently diagnostic and used in a more optimal manner, and this is yet another technical effect.

Frame rates in the temporal dimension of 4D reconstruction are essentially limitless, bounded only by the number of available views. This advantage and technical effect can be beneficial to precise radiation therapy planning. The flexibility offered allow for either full-scan or half-scan approaches for multiple images.

Another technical effect is that data usefulness can be assessed at the scanner console while the patient is still available. When aberrant respiratory waveforms are observed, an additional, corrective scan (only at desired table location(s)) may be acquired, thus limiting incomplete datasets and non-diagnostic image generation.

Processing 4DCT data on the console makes feasible the ability to prospectively verify the quality of the 4D data set, thus reducing dose considerably by minimizing potential for rescanning patients.

This approach provides flexibility to create a 4D series based on any trigger points in the respiratory signal, if a method other than phase grouping is preferred (such as motion or amplitude), then the method is easily adaptable to the timepoints of any periodic waveform-based trigger. For example, the waveform can be a cardiac waveform. Additionally, the trigger need not be by phase. For example, in one embodiment, instead of phase binning, amplitude binning is done. In amplitude binning, the image generation triggers are based on amplitude values of the recorded respiratory waveform. These amplitude-based triggers do not necessarily line up with phase-based triggers.

The herein described methods and apparatus are an important development in supporting the demands of dynamic imaging technologies. The method approaches respiratory-gated imaging by driving the reconstruction process with the respiratory waveform. This technique creates a platform for extremely flexible data manipulation and processing. The many advantages listed above are realized through this approach.

Technical effects include generating volumetric image data at multiple phases in a periodic respiratory cycle. Images are generated based on precise timing of an input signal. Images are specified by a target view location (and range of view data) in the scan data. The temporal resolution of 4DCT is significantly improved. More frequent clinical usability of 4DCT scan data is hereby provided. Detection and correction of aberrant images in the 4D acquisition is also hereby provided. Half-scan, full-scan, or overlapping image generation from scan data is also hereby provided.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:
1. A method comprising:
  receiving cine scan data;

receiving a plurality of target phases of a periodic waveform;

generating a plurality of images, each image centered at one of the received target phases;

performing a waveform analysis on the periodic waveform to detect an aberration; and shifting the center of at least one image to correct for the detected aberration.

2. A method in accordance with claim 1 wherein the periodic waveform is a respiratory waveform.

3. A method in accordance with claim 1 wherein the periodic waveform is a cardiac waveform.

4. A method in accordance with claim 1 further comprising prompting a user when an aberration is detected.

5. A method comprising:

performing a waveform analysis to detect an aberration;

prompting a user when an aberration is detected; and shifting the center of at least one image to correct for the detected aberration.

6. A method in accordance with claim 5 wherein said prompting comprises prompting a user that is acquiring cine scan data.

7. A method in accordance with claim 6 wherein said prompting comprises prompting a user that is acquiring cine scan data to determine if a re-acquisition of the data is desired where the aberration occurred.

8. A method in accordance with claim 5 wherein said prompting comprises prompting a user that is at a workstation remote from a system that acquired cine scan data.

9. A method in accordance with claim 5 wherein said prompting comprises prompting with regards to shifting cine scan data.

10. A method in accordance with claim 9 wherein said prompting comprises prompting a user that is at a workstation remote from a system that acquired cine scan data.

11. A method in accordance with claim 5 wherein said performing comprises performing a waveform analysis on a waveform extracted from cine scan data.

12. A method in accordance with claim 5 wherein said performing comprises performing a waveform analysis on a waveform not extracted from cine scan data.

13. A system for reconstructing images, said system comprising:

a radiation source;

a radiation detector positioned to receive radiation emitted from said source; and a computer coupled to said source and said detector, said computer configured to:

receive scan data from said detector;

perform a temporal synchronization of the scan data using a waveform received from an external device or other means of quantifying periodic motion;

perform a waveform analysis to detect an aberration; and shift the center of at least one image to correct for the detected aberration.

14. A system in accordance with claim 13 wherein the waveform is a respiratory waveform.

15. A system in accordance with claim 14 wherein the temporal synchronization is the temporal synchronization to target phases received from a user.

16. A system in accordance with claim 15, wherein said computer is further configured to prospectively gate acquisitions around the target phases.

17. A method comprising:

receiving at least one target phase;

scanning a periodic moving object to obtain at least one complete waveform of the periodic motion;

using the waveform to prospectively gate acquisitions around the target phase;

performing a waveform analysis to detect an aberration; and shifting the center of at least one image to correct for the detected aberration.

18. A method in accordance with claim 17 wherein the periodic moving object is a pair of lungs and the waveform is a respiratory waveform.

* * * * *